United States Patent [19]

Liotta

[11] Patent Number: 4,837,145

[45] Date of Patent: Jun. 6, 1989

[54] LAYERED IMMUNOASSAY USING ANTIBODIES BOUND TO TRANSPORT PARTICLES TO DETERMINE THE PRESENCE OF AN ANTIGEN

[76] Inventor: Lance A. Liotta, 9027 Mistwood Dr., Potomac, Md. 20854

[21] Appl. No.: 871,857

[22] Filed: Jun. 9, 1986

[51] Int. Cl.$^4$ .............................................. G01N 33/53
[52] U.S. Cl. ......................................... 435/7; 422/55; 422/56; 422/58; 422/60; 435/287; 435/288; 435/310; 436/523; 436/541; 436/807; 436/819; 436/824; 436/828
[58] Field of Search ................... 435/7, 287, 310; 436/810, 819, 825, 828, 523, 533, 534, 541; 422/56, 61

[56] References Cited

U.S. PATENT DOCUMENTS

| | | | |
|---|---|---|---|
| 4,459,358 | 7/1984 | Berke | 436/810 |
| 4,459,361 | 7/1984 | Gefter | 436/523 |
| 4,666,863 | 5/1987 | Edwards et al. | 436/533 |

*Primary Examiner*—Sam Rosen
*Attorney, Agent, or Firm*—Fay, Sharpe, Beall, Fagan, Minnich & McKee

[57] ABSTRACT

A device is provided for determining the presence of an antigen which comprises a trapping zone, which contains material capable of capturing free flowing enzyme linked antibodies, but not antibodies bound to a transport particle which flows freely through the trapping zone into the substrate zone, and a substrate zone which contains material capable of reacting with enzyme-linked antibodies to produce a reaction which indicates the presence of antibodies. A method of determining the presence of an antigen is provided wherein a sample is mixed with two classes of antibodies which are specific for the antigen being tested for, but which react with different antigen domains, wherein the mixture consists of class one antibodies bound to a transport particle which flows freely through the trapping zone and class two enzyme-linked antibodies which are incapable, unless bound to the transport particles, of flowing freely through the trapping zone. In the presence of the antigen being tested for, both classes of antibodies bind to the antigen and flow through the trapping zone into the substrate zone, wherein a reaction takes place to indicate the presence of the antigen.

16 Claims, 3 Drawing Sheets

LAYERED IMMUNOASSAY USING ANTIBODIES BOUND TO TRANSPORT PARTICLES TO DETERMINE THE PRESENCE OF AN ANTIGEN

BACKGROUND OF THE INVENTION

The invention relates to a method and device for determining the presence of an antigen in test samples through the use of a specially designed enzyme labeled "double site" immunoassay technique.

Enzyme labeled immunoassay employing antibodies which react with different domains on the same antigen have been described in the scientific literature. In general, all such "double site" immunoassays are conducted as follows: One member of the antibody pair is fixed to a solid support such as the wall of a plastic tube or the surface of a plastic stick. The second antibody is conjugated with an enzyme label. The antigen containing sample and the second antibody conjugate are mixed together with the first antibody bound to the solid support. In the presence of the antigen the antibody conjugated becomes bound to the solid support via the opposite member of the antibody pair.

The solid support is then washed thoroughly to remove any unbound conjugate. Finally the solid support is incubated with a color forming enzyme substrate. The color reaction can then be read visually or with an instrument to indicate the presence and quantity of the antigen. Such two site immunoassays can be specific and rapid but require multiple washing and color forming incubation steps.

The present invention is a two site immunoassay which has no washing or separate color reaction steps. The antigen containing sample is mixed with the two antibody reagents and the mixture is applied to the surface of a two layered test device. The bottom layer contains the color forming substrate. In the presence of the antigen the conjugate is carried to the bottom layer and produces a color reaction. In the absence of the antigen all the conjugate is trapped in the solid phase top trapping layer and fails to reach the lower color forming layer. The principle of the invention is exactly the opposite of the previous two site immunoassays, because the conjugate which fails to bind the antigen is trapped on the solid phase. The conjugate which binds to the antigen washes through the solid phase zone to the color forming layer.

The foregoing and other advantages of the instant invention will become apparent to those skilled in the art from a reading of the following specification and claims.

SUMMARY OF THE INVENTION

In one aspect, the present invention concerns a device for determining the presence of an antigen which comprises a trapping zone containing a material capable of capturing free flowing enzyme-linked antibodies, but not antibodies bound to a transport particle which flow freely through the trapping zone into the substrate zone, and a substrate zone which contains material capable of reacting with the enzyme-linked antibodies to produce a reaction which indicates the presence of the enzyme and therefor the concerned antigen.

In another aspect, the instant invention is directed to a unique method for determining the presence of antigens in a sample which comprises the steps of bringing the sample into contact with two classes of antibodies which are specific for the antigen being tested for, but wherein each class of antibodies reacts with a different domain in the antigen to produce a complex which is capable of flowing through the trapping layer to produce a reaction in the substrate layer which indicates the presence of the antigen being tested for.

DESCRIPTION OF THE DRAWINGS

The following is a brief description of the drawings which are presented for the purpose of illustrating the invention and not for the purpose of limiting the same.

Figure 1:
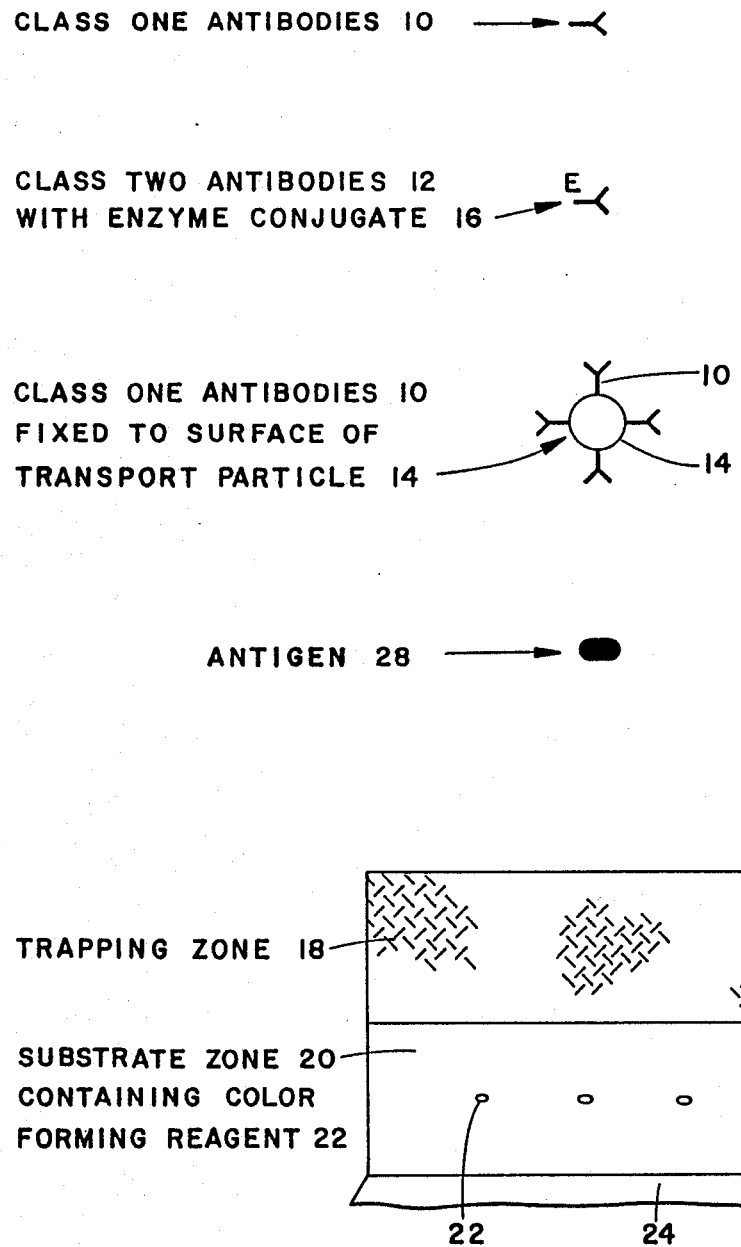
FIG. 1 is a diagrammatical illustration of the device A of the present invention. It includes two distinct layers, viz., a trapping zone 18 and substrate zone 20. Class one antibodies 10 and class two antibodies 12 are shown positioned in close proximity to device A. Class one antibodies 10 are fixed to the surface of transport particles 14, and class two antibodies 12 are conjugated to enzymes 16.

Trapping zone 18 is fashioned from a porous material which captures class two antibodies 12 conjugated with enzyme 16, but fails to capture transport particles 14 which are bound with class one antibodies 10. Substrate zone 20, likewise, is fabricated from a porous material and contains a bound color-forming reagant 22, i.e., a material which reacts with enzyme 16 conjugated to class two antibodies 12 to produce a color. The device A is shown on a supporting member 24.

Figure 2:
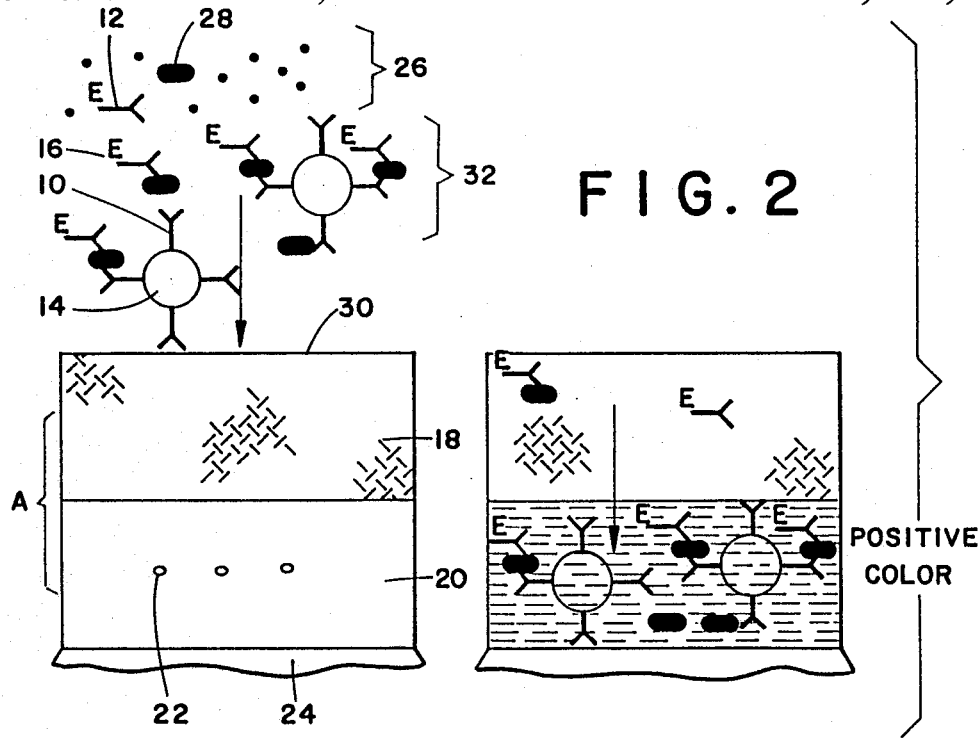

FIG. 2 is a diagrammatical illustration showing the method of the invention using device A of FIG. 1. Specifically, a fluid, generally identified by numeral 26, containing free antigen 28, is mixed with class one antibodies 10 bound to transport particles 14, and class two antibodies 12 conjugated with enzyme 16. Class one antibodies 10 bound to transport particles 14 bind with specific recognition sites on antigens 28. Similarly, class two antibodies 12 conjugated with enzyme 16 bind with alternative specific receptor sites on antigens 28 are attached to class one antibodies 10 which, in turn, are bound to transport particles 14 thereby forming resulting complexes 32. As the fluid diffuses through trapping zone 18 all class two antibodies 12 conjugated with enzyme 16 which have not formed resulting complexes 32, are captured in trapping zone 18, while all class two antibodies 12 conjugated with enzyme 16 which have formed resulting complexes 32 flow through the trapping zone 18 into the substrate zone 22 where the conjugated enzyme 16 reacts with the color forming reagent 22 to produce a distinctive color which indicates the presence of antigen 28 in the applied fluid 26.

Figure 3:
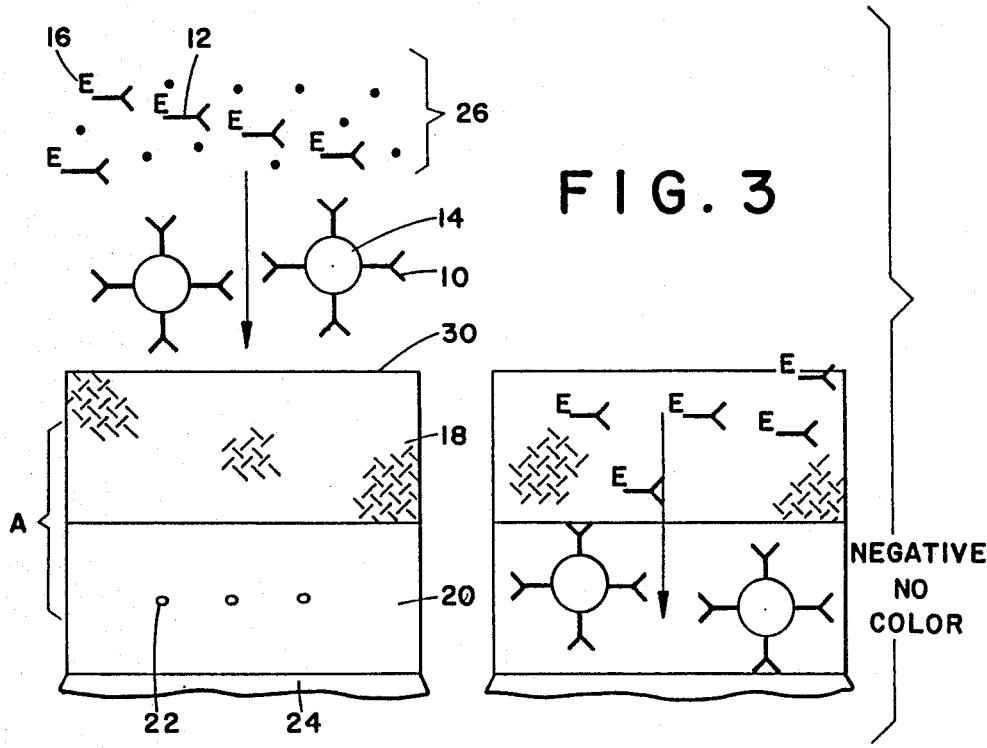

FIG. 3 is a diagrammatical illustration showing the method of the invention using device A of FIG. 1 and showing the results obtained when the test fluid 26 is devoid of antigen 28. Specifically, a fluid, generally designated 26, is applied to the surface 30 of trapping zone 18. As the fluid diffuses through trapping zone 18, all of the class two antibodies 12 conjugate with enzyme 16 are captured by trapping zone 18. Accordingly, no enzyme-linked antibodies reach the color forming reagent 22 in substrate zone 20 and no color change is observed, indicating the absence of antigen 28 in test fluid 32.

Figure 4:
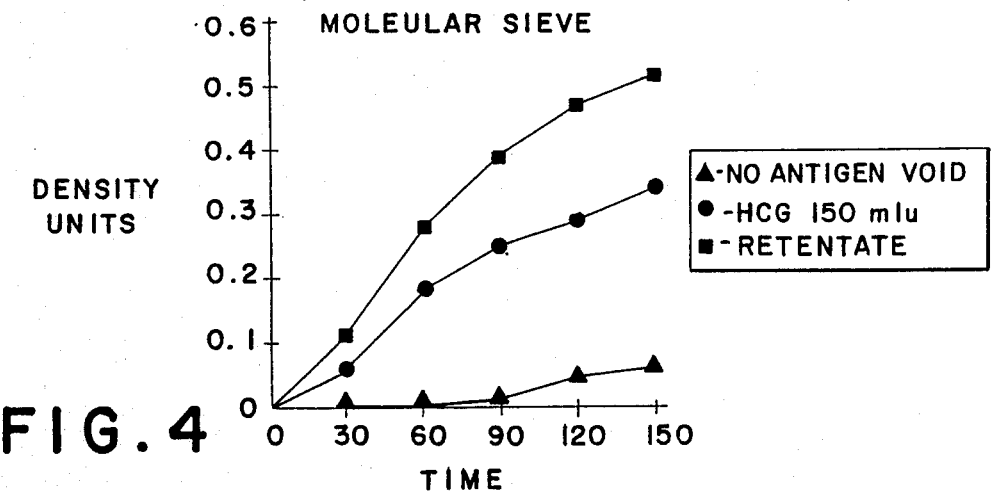

FIG. 4 shows the trapping of the free enzyme-antibody conjugate by using molecular sieve material as the trapping layer.

Figure 5:
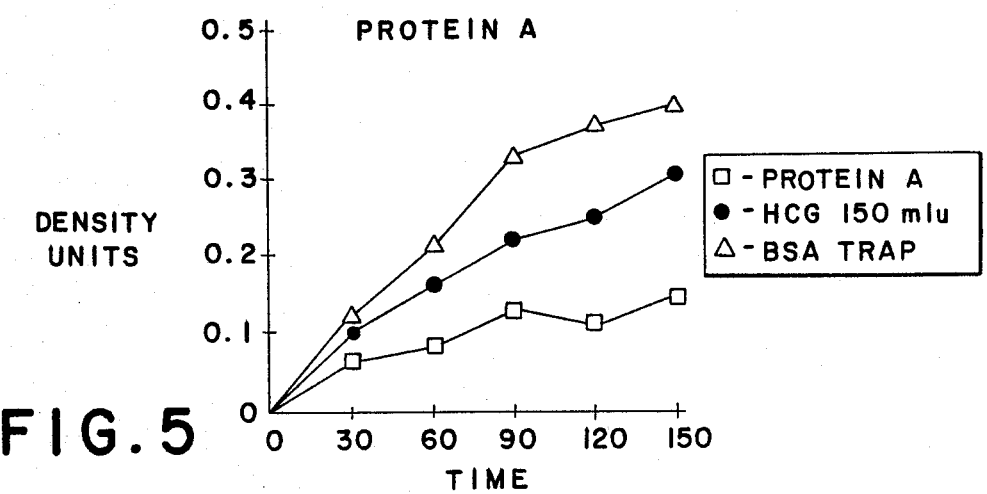

FIG. 5 shows the trapping of the free enzyme-antibody conjugate by using Protein A nitrocellulose as the trapping layer.

Figure 6:
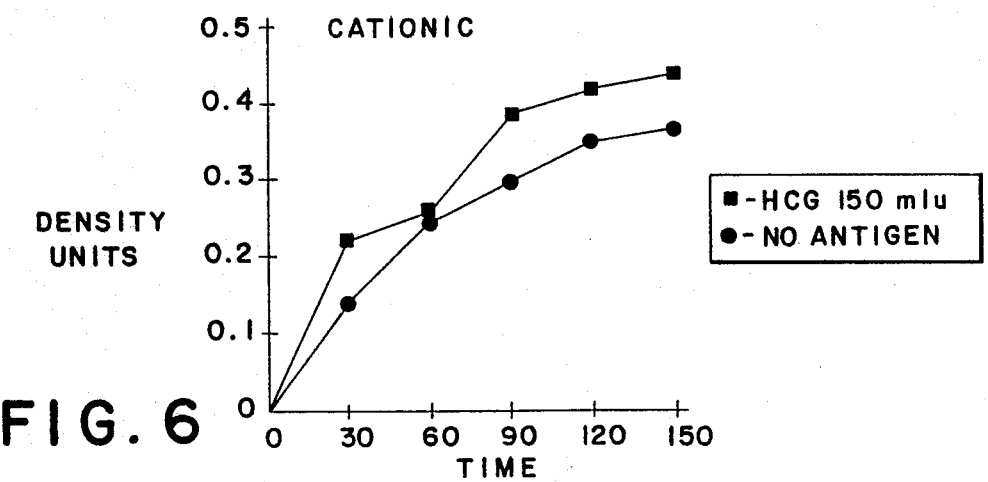

FIG. 6 shows the trapping of the free enzyme-antibody conjugate through the use of a cationic exchange resin as the trapping layer.

DESCRIPTION OF THE PRACTICE OF THE INVENTION

The present invention involves use of the following elements: class one and class two antibodies which recognize different sites on the same antigen; a transport particle upon which antibodies of class one are fixed; enzymes conjugated to the class two antibodies; and an immunoassay device consisting of a trapping zone which binds antibodies of class two but not antibodies of class one, and a substrate zone which reacts with the enzyme conjugated to class two antibodies to produce a distinctive color (see FIG. 1).

The antibodies consist of class one antibodies which are attached to a transport particle and class two antibodies which are conjugated to a label such as an enzyme. While both classes of antibodies are specific for the same antigen, different epitopes, or binding sites, are recognized by each class of antibodies. Thus, each class of antibodies can attach to the same antigen, facilitating the usage of a double site immunoassay.

The basic concept of the present invention centers upon the interrelationship of the transport particle, the two classes of antibodies, and an immunoassay device which consists of layered trapping and substrate zones. The trapping zone is highly specific for the free antibody conjugate consisting of class two antibodies, while the transport particle passes freely between the two layers. The substrate zone produces a color forming reaction in the presence of the enzyme.

When the two classes of antibodies are mixed with an antigen free sample, and this mixture is placed in contact with the layered trapping and substrate zones, no color change is observed (see FIG. 3). As the result of the absence of antigen, double site recognition can not occur and all of the indicative class two free antibody conjugate are captured by the trapping zone. Thus, no enzyme substrate reaction transpires and no color change is observed.

However, in the presence of an antigen containing sample, the conjugate class two antibodies become linked to the transport particle through the antigen (see FIG. 2). As a result of the double site recognition, the antibody conjugate enzyme cannot be captured in the trapping zone because the transport particle protects the conjugate from being captured by the trapping layer. Thus the transport particle carries the conjugate to the color forming layer only if the antigen is present.

In the preferred practice of the invention the antibodies utilized consist of two classes of antibodies which are specific for the antigen being tested for. However, each class of antibody is highly specific for different recognition sites or epitopes on the antigen in question so that no cross reactivity or overlap can occur. Moreover, both classes of antibodies which are specific for the antigen being tested for may be found in the trapping zone of the device, eliminating the need of any pre-application mixing.

The materials used to construct the device of the present invention are well known in the art. The trapping layer can be any molecular sieve material which captures the small molecular weight conjugate but fails to capture the transport particle.

The trapping mechanism may be based upon, but not limited to, size, i.e. through the use of molecular sieve particles containing small crevices which trap only the small antibody enzyme conjugates and not the transport particle complexes which are too large to enter the crevices of the molecular sieve material; charge, i.e. the antibody-enzyme conjugate binds to oppositely charged groups found in the trapping zone which the transport particle fails to bind because its average charge is different from that of the material found in the trapping zone or in the test solution, and because the transport particle mass is much greater than the other proteins; and by the proteins own natural affinites for their binding sites, i.e. Protein A will only bind to the Fc portion of the antibodies, thus when the Fc portions of the antibodies are bound to the surface of the transport particle, it becomes physically impossible for Protein A to be bound to said antibodies, thus allowing the transport particle complex to flow through the trapping zone while capturing the free flowing antibodies.

Examples of suitable solid phase material for the construction of the trapping zone include resin and fibrous materials, agrose gels and any other material containing sufficient void volumes to trap the free flowing antibodies but not the transport particles.

In addition, suitable substrates or color-forming reagents utilized in the present invention are also well known in the art. In this regard, a number of different types of purified enzymes which act directly or indirectly with the color forming agent found in the substrate may be utilized. An example of such an enzyme and its corresponding substrate is horseradish peroxyidase and p-nitrophenylphosphate. The antibodies can also be labelled with radioactive or floursescent markers.

In one embodiment of the invention, the physical binding of the conjugate to the transport particle protects it from binding to a protein A fixed on the surface of the trapping layer. The means by which the trapping layer captures the conjugate is not limited to these specific embodiments. Other alternative means such as biotin-avidin complex formation may also be utilized.

However, the present invention is not limited to the use of this enzyme and its corresponding substrates. Other enzyme-substrate combinations well known in the art may also be utilized.

The transport particle can also be fabricated in a variety of ways. For example, the transport particle can be a colloidal substance of a high molecular weight such as dextran, solid particles composed of plastic, glass, resin or metallic materials, or a high molecular weight polymer. In addition, the transport particle can also express a net anionic surface change which protects the conjugate from being captured by a cationic charge on the trapping layer.

The instant invention will now be further described with reference to the following Example.

EXAMPLE

Test: To determine the feasibility of utilizing the present invention for pregnancy detection through the detection of human chorionic gonadotrophin (HCG) antigen.

Materials Utilized:

A. Antigen: human chorionic gonadotrophin (HCG) from positive urine control Pregnospia Kit 150 mIU/ml.

B. Antibodies:

(i) class one antibodies attached to transport particles; Mouse monoclonal antibodies against HCG (Lot 4284148 Supplied lypholized) bound to pregnospia colloidal gold particles.

(ii) class two antibodies conjugated with enzyme: Anti HCG Miles Yeda Inc. (lot 1064 beta subunit specific source ascites PC-2 clone)
Peroxidase concentration 0.53 mg/ml
Mouse IgG 1.01 mg/ml
Affinity $5.3 \times 10^{10}$ leaders/mole C. Trapping Zones
  A. Preswollen Sephadex G-100 M packed in a conical chamber 0.4 cm top, 0.4 cm high, 0.1 cm botton, volume 75 microliters.
  B. Nitrocellulose 5 micrometer pore size, Millipore, 4 layers stacked in immunowell template coated with Protein A (S. aureus, Cowan Strain, Vector Labs) 10 mg/ml blocked with BSA
  C. Cationic resin (Beckman FPLC Mono C) prepared as in A) above.
  D. Color forming enzyme substrate: glucose oxidase 2.0 mg/ml+tetramethylbenzidine (TMB) 20.0 mg/ml dissolved in absolute methanol air dried on Whatman No. 5 paper.

Procedure

Step 1: Preparation of the two classes of antibodies and their attached agents:
  Class one antibodies, consisting of monoclonal antibodies against a specific receptor site on the HCG antigen, are attached to transport particles consisting of pregnospia colloidal gold particles.
  Class two antibodies, consisting of monoclonal antibodies beta subunit specific which recognize a different domain on the HCG antigen than the class one antibodies are conjugated to horseradish peroxidase (HRP).

Step 2: Preparation of various immunoassay devices. Three types of immunoassay were employed (of type described herein before under heading "Trapping Zones"). Each utilized a different type of trapping zone which was placed on top of the substrate layer by methods known in the art.

Step 3: The test solution is mixed with the two classes of antibodies. The mixture is then placed in contact with the surface layer of the various immunoassay devices.

RESULTS

FIG. 4 shows the trapping of the free conjugate by the molecular sieve zone. In the absence of antigen no significant color formation was observed for a dilution of 1/1000 and a volume of 100 microliters. Applied directly to the substrate layer a color density of 0.47 du was illicited within 2 minutes. In the presence of preincubation for 2 minutes with the antigen a significant color reaction of 0.31 du was illicited.

FIG. 5 shows the embodiment using the Protein A nitrocellulose trapping layer. The trapping layer was moderately efficient. In the absence of antigen only a color of 0.13 due above background was illicited. In the presence of the antigen the color signal was 0.25 du indicating that binding of the conjugate to the transport particle clearly protected it from being trapped by the protein A.

FIG. 6 shows the use of cationic exchange resin as the trapping layer. This embodiment was less efficient than the others mentioned above but it served to determine the presence or absence of antigen. In the absence of the antigen significant color was produced at all antibody dilutions. In the presence of the antigen a quantitative increase in color was observed indicating that the transport particle afforded some protection from binding to the resin.

From the foregoing it is clear that the device and method of the present invention is quite effective in the determination of whether a specific antigen exists in a given test sample. The numerous applications to which the present invention may be put are readily apparent to those skilled in the art to which the invention pertains.

While there has been described what are at present considered to be the preferred embodiments of this invention, it will be obvious to those skilled in the art that various changes and modifications may be made therein without departing from the invention, and it is, therefore, intended in the appended claims to cover all such changes and modifications as fall within the true spirit and scope of the invention.

What we claim is:

1. A device for determining the presence of antigens in a sample which comprises:
  (a) an upper trapping zone containing material capable of capturing free flowing enzyme-linked class two antibodies, but not class one antibodies bound to a transport particle which flows freely through said trapping zone, wherein said class one antibodies and said class two antibodies are both specific to an antigen being tested for with said class one antibodies and said class two antibodies recognizing different domains on said antigens, wherein said class one antibodies are bound to a transport particle and said class two antibodies are free flowing antibodies linked to an enzyme, whereby in the presence of the antigen being tested for, the class one antibodies and the class two antibodies form complexes with said antigens comprised of the class one antibodies bound to a transport particle, the antigen being tested for, and the class two enzyme-linked antibodies; and,
  (b) a lower substrate zone containing material capable of reacting with the enzyme-linked class two antibodies attached to the class one antibodies bound to the transport particle of said complexes by means of the antigen being test for to produce a reaction which indicates the presence of said antigens in the sample.

2. The device of claim 1 wherein said reaction in the substrate zone which indicates the presence of said enzyme-linked class two antibodies attached to the class one antibodies bound to the transport particle of said complexes by means of the antigen being tested for is a color forming reaction.

3. The device of claim 1 wherein said trapping zone is fabricated from nitrocellulose coated with Protein A.

4. The device of claim 1 wherein said trapping zone is fabricated from agrose gel.

5. A device for determining the presence of antigens in a sample which comprises:
  (a) an upper trapping zone containing (i) class one antibodies and class two antibodies, both of which are specific for the antigen being tested for but which recognize different domains on the antigen, with the class one antibodies being bound to a transport particle and the class two antibodies being free flowing and linked to an enzyme, whereby in the presence of the antigen being tested for, the class one antibodies and the class two antibodies form complexes with said antigen being tested for within the trapping zone including class one antibodies bound to a transport particle, the antigen, and class two enzyme-linked antibodies, and (ii) material capable of capturing the free flowing class two antibodies but not the class one antibodies or any other substance bound to said transport particle; and (b) a lower substrate zone containing material capable of reacting with the enzyme linked class two antibodies attached to the class one antibodies bound to the transport particle of said complexes by means of the antigens being tested for to produce a reaction which indicates the presence of said antigens in the sample.

6. The device of claim 5 wherein said reaction in the substrate zone which indicates the presence of said enzyme-linked class two antibodies attached to the class one antibodies bound to the transport particle of said complexes by means of the antigen being tested for is a color forming reaction.

7. The device of claim 5 wherein said trapping zone is fabricated from nitrocellulose coated with Protein A.

8. The device of claim 5 wherein said trapping zone is fabricated from agrose gel.

9. A method for determining the presence of an antigen in a test sample comprising the steps of:

(a) bringing the test sample into contact with a mixture of class one and class two antibodies both of which are specific to said antigen but which each recognize different domains on said antigen, with said class one antibodies being bound to a transport particle and said class two antibodies being linked to an enzyme, whereby in the presence of said antigen, complexes are formed within said mixture which include class one antibodies bound to a transport particle, the antigen, and class two enzyme-linked antibodies;

(b) bringing said mixture into contact with a device comprising an upper trapping zone and a lower substrate zone, wherein said upper trapping zone contains material capable of capturing free antibodies including unbound enzyme-linked class two antibodies but not class one antibodies bound to a transport particle or any other substance bound to said transport particle including said complexes, and wherein said lower substrate zone contains material capable of reacting with said enzyme to indicate the presence of said enzyme-linked class two antibodies;

(c) allowing said mixture to permeate through said upper trapping zone, wherein all antibodies bound to said transport particles, including said complexes, flow freely through said upper trapping zone into the lower substrate zone, while all antibodies not bound directly or indirectly to said transport particles, including free flowing enzyme-linked class two antibodies are captured by said upper trapping zone; and, (d) observing the presence or absence of any change in said lower substrate zone to thereby determine the presence or absence of the tested for antigen in said sample.

10. The method of claim 9, wherein said change in the substrate zone to thereby determine the presence or absence of the tested for antigen in said sample is caused by a color change.

11. The method of claim 9, wherein said trapping zone is fabricated from nitrocellulose.

12. The method of claim 9, wherein the antigen being determined is human chorionic gonadotrophin.

13. A method for determining the presence of an antigen in a test sample comprising the steps of:

(a) bringing the test sample into contact with a device containing (i) an upper trapping zone containing class one and class two antibodies both of which are specific to the antigen but which recognize different domains on the antigen, with the class one antibodies being bound to a transport particle and the class two antibodies being linked to an enzyme, whereby in the presence of the antigen being tested for, the class one and the class two antibodies form complexes with said antigen within the upper trapping zone comprising class one antibodies bound to a transport particle, the antigen, and class two enzyme-linked antibodies, and wherein said upper trapping zone contains material capable of capturing the class two antibodies, but not the class one antibodies or any other substance bound to said transport particles, and (ii) a lower substrate zone containing material capable of reacting with the enzyme-linked class two antibodies to produce a reaction which indicates the presence of said antibodies;

(b) allowing said mixture to permeate through said upper trapping zone, wherein all antibodies bound to said transport particles, including the complexes, flow freely through said upper trapping zone into the lower substrate zone, while all antibodies not bound to said transport particles, including free flowing enzyme-linked class two antibodies are captured by said upper trapping zone; and, (c) observing the presence or absence of any change in said lower substrate zone to thereby determine the presence or absence of the tested for antigen in said sample.

14. The method of claim 13, wherein said change in the substrate zone to thereby determine the presence or absence of the tested for antigen in said sample is caused by color change.

15. The method of claim 13, wherein said trapping zone is fabricated from nitrocellulose.

16. The method of claim 13, wherein the antigen being determined is human chorionic gonadotrophin.

* * * * *